United States Patent [19]

Vanlerberghe et al.

[11] Patent Number: 4,666,711

[45] Date of Patent: May 19, 1987

[54] NON-IONIC SURFACE-ACTIVE AGENTS AND COMPOSITIONS IN WHICH THEY ARE PRESENT

[75] Inventors: Guy Vanlerberghe, Claye-Souilly; Henri Sebag, Paris, both of France

[73] Assignee: L'Oreal, Paris, France

[21] Appl. No.: 777,251

[22] Filed: Sep. 18, 1985

Related U.S. Application Data

[63] Continuation of Ser. No. 548,162, Nov. 2, 1983, abandoned, which is a continuation of Ser. No. 188,022, Sep. 17, 1980, abandoned.

[30] Foreign Application Priority Data

Sep. 18, 1979 [FR] France ................................ 79 23253

[51] Int. Cl.$^4$ ...................... C07C 43/11; C07C 43/15; A61K 7/42; A61K 7/06
[52] U.S. Cl. ......................................... 424/70; 424/59; 514/845; 514/846; 514/847; 514/941; 568/27; 568/45; 568/46; 568/50; 568/59; 568/614; 568/616; 568/623
[58] Field of Search ................... 568/614, 616, 27, 45, 568/46, 50, 59, 623; 424/70, 59; 514/845, 846, 941, 847

[56] References Cited

U.S. PATENT DOCUMENTS

| | | | |
|---|---|---|---|
| 3,595,924 | 7/1971 | Kalopissis et al. | 568/614 X |
| 3,840,606 | 10/1974 | Vanlerbergh | 568/614 X |
| 3,879,471 | 4/1975 | Farber | 568/45 |
| 3,906,048 | 9/1975 | Vanlerberghe et al. | 568/45 |
| 3,959,390 | 5/1976 | Vanlerbergh | 568/614 |
| 4,138,427 | 2/1979 | Vanlerbergh et al. | 568/614 X |

Primary Examiner—Bernard Helfin
Attorney, Agent, or Firm—Cushman, Darby & Cushman

[57] ABSTRACT

The invention relates to non-ionic surface-active agents which correspond to the formula

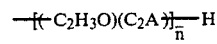

in which R denotes a linear or branched, saturated or unsaturated aliphatic radical containing 4 to 20 carbon atoms, $R_1$ denotes (1) a, preferably linear, alkyl radical, (2) a linear or branched alkoxymethyl radical or (3) an alkenyloxymethyl radical, the alkyl or alkenyl parts of these radicals containing from 4 to 20 carbon atoms, and Z denotes a polyether linkage corresponding to the formula $$-(C_2H_3O)(C_2A)_{\overline{n}}-H$$

in which $\overline{n}$ denotes an average statistical value of 2 to 20 and A denotes
(a) the group OH,
(b) the group

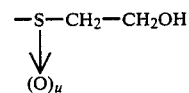

in which u denotes 0 or 1, or
(c) the group

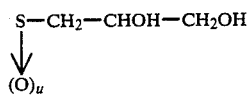

in which u dentoes 0 or 1, the radicals R and $R_1$ containing a total of 12 to 38 carbon atoms, as well as to the derivatives of the above compounds which result from the reaction of ethylene oxide or glycidol with the OH groups.

These compounds can be used, in particular, as base surface-active agents or as additives in cosmetic or pharmaceutical compositions.

6 Claims, No Drawings

NON-IONIC SURFACE-ACTIVE AGENTS AND COMPOSITIONS IN WHICH THEY ARE PRESENT

This is a continuation of application Ser. No. 548,162, filed Nov. 2, 1983 which is a continuation of Ser. No. 188,022, filed Sept. 17, 1980, both now abandoned.

The present invention relates to non-ionic surface-active agents, the process for their preparation and compositions containing them.

In recent years, one of the great preoccupations of laboratories preparing compositions intended for the care and treatment of the skin and hair has been to find surface-active agents which can be used as base products, as vehicles for active products, as excipients or as additives, which are perfectly tolerated by man.

We have already proposed a number of surface-active products, in particular non-ionic surface-active agents, which represent an advance compared with the existing products. In particular French Specification No. 2,401,187, describes the preparation of surface-active block oligomers consisting of a series of lipophilic units and a series of hydrophilic units; these are, in particular, less agressive than previous products. These compounds also possess surface and solubility properties which are satisfactory for the applications envisaged.

However, we have realised that, for developing different formulations, the properties obtained with this type of compound are sometimes inadequate, more precisely as regards their behaviour in water or in an aqueous-alcoholic medium.

The expression "behaviour in water" is used to mean the solubility or dispersibility in this medium, or also the formation of lyotropic mesomorphic phases which are more homogeneous and more favourable for the preparation of oil-in-water or water-in-oil emulsions, or of lipid membranes which are capable of transporting active substances.

In particular, for certain cosmetic or pharmaceutical compositions, it is frequently a very appreciable advantage to be able to reduce the proportion of alcoholic compounds in the formulation by increasing the solubility of the compounds in water.

We have now discovered, according to the present invention, surface-active compounds which, from precisely these points of view, possess improved properties compared with the products described previously. These compounds are more readily dispersible in water or more completely soluble, and generally possess better emulsifying properties.

Furthermore, they greatly facilitate the formation of lipid membranes suitable for the transport of active molecules. For products soluble in aqueous-alcoholic solutions, the alcohol concentration can be lowered substantially by using the compounds according to the invention.

The compounds according to the invention comprise a lipophilic part consisting of two fatty chains, which is joined to a hydrophilic part containing ether and hydroxyl groups and optionally thioether and/or sulphoxide groups. We have found that, by separating off and purifying the lipophilic part consisting of the two fatty chains, products can be obtained which possess improved properties, such as those indicated above, in particular as regards purity and solubility, without loss in the surface activity or in the biological properties, compared with compounds of the same type in which the lipophilic part contains variable numbers of fatty chains, these numbers being statistically distributed around an average value of between 2 and 10.

The present invention thus relates, in particular, to polyhydroxylic polyether surface-active agents with two hydrocarbon chains, to the preparation of these compounds and to cosmetic or pharmaceutical compositions intended for the care and treatment of the body or head of hair, which contain these surface-active compounds.

The surface-active compounds according to the invention are essentially characterised in that they correspond to the formula I:

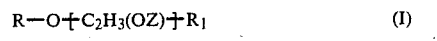

in which R denotes a linear or branched, saturated or, generally ethylenically, unsaturated aliphatic radical containing 4 to 20 carbon atoms, $R_1$ denotes (1) a, preferably linear, alkyl radical, (2) a linear or branched alkoxymethyl radical or (3) an alkenyloxymethyl radical, the alkyl or alkenyl parts of these radicals containing from 4 to 20 carbon atoms, and Z denotes a polyether linkage corresponding to the formula

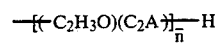

in which $\bar{n}$ denotes an average statistical value of 2 to 20 and A denotes
(a) the group OH,
(b) the group

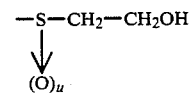

in which u denotes 0 or 1, or
(c) the group

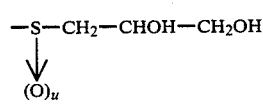

in which u denotes 0 or 1.

The radicals $R_1$ and R must contain a total number of carbon atoms of 12 to 38 and preferably 12 to 32; R preferably denotes a linear or branched hydrocarbon radical chosen, in particular, from butyl, hexyl, octyl, decyl, dodecyl, tetradecyl, hexadecyl, octadecyl, 2-ethylhexyl and 2-hexyldecyl groups, and $R_1$ preferably denotes a radical chosen from hexyl, octyl, decyl, dodecyl, tetradecyl, hexadecyl and octadecyl groups, alkoxymethyl radicals derived from the above groups, or also 2-ethylhexyloxymethyl, 2-hexyldecyloxymethyl or 2-octyldodecyloxymethyl radicals.

The compounds of the formula I can be prepared in accordance with a three-step process. The compounds of the formula II:

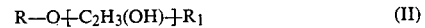

in which R and $R_1$ have the same meanings as those indicated above, are initially prepared, in a first step, by reacting an alcohol of the formula ROH with a compound having a terminal epoxide group, of the formula $$R_1-CH-CH_2 \atop \diagdown O \diagup \qquad (III)$$

in which formulae the groups R and $R_1$ have the same meanings as those indicated above. This reaction is carried out in the presence of a Lewis acid catalyst, such as boron trifluoride, stannic chloride or antimony pentachloride, generally in an amount of 0.2 to 5% by weight, relative to the reaction mixture, and at a temperature from 20° to 120° C. and preferably 50° to 100° C. It can also be carried out in the presence of an alkali metal catalyst, such as sodium or potassium or the methylate, ethylate or tert.-butylate of sodium or potassium, generally in an amount of 0.2 to 15%, and preferably 0.5 to 10%, relative to the reaction mixture, and at a temperature from 100° to 180° C. and preferably 100° to 150° C.

The reaction should be carried out with stoichiometric proportions of the alcohol ROH and of the epoxide compound, or, preferably, in the presence of an excess of one of the two reactants. When the alcohol is used in excess, the unreacted alcohol is removed by distillation. When, on the other hand, the epoxide is in excess, it reacts completely to give alcohol compounds with several lipophilic chains.

It is also possible to use an aliphatic or aromatic hydrocarbon as the solvent, although this is not generally necessary. In all cases, the compounds of the formula (II) can be purified by conventional distillation under reduced pressure or by molecular distillation.

Depending on the way in which the epoxide ring opens, one of two possible structures are obtained for the compounds of the formula (II):

$$R-O-CH_2-CH-R_1 \quad \text{or} \quad R-O-CH-R_1 \atop \qquad\qquad\quad OH \qquad\qquad\qquad\qquad CH_2OH$$

(IIA) \qquad\qquad\qquad (IIB)

In the second step, the compounds of the formula (IV):

$$R-O+C_2H_3(OY)+_{\overline{n}}R_1 \qquad (IV)$$

in which R and $R_1$ have the meanings indicated above and Y denotes a polyether linkage of the formula $$+C_2H_3O(CH_2B)+_{\overline{n}}$$

in which B denotes a halogen atom or a tert.-butoxy group, n having the same meaning as above, are obtained by carrying out a polyaddition reaction of an epihalogenohydrin or tert.-butyl glycidyl ether with a fatty alcohol having two lipophilic chains, of the formula II, these intermediates being converted to the compounds of the formula (I) in accordance with processes which are in themselves known.

More particularly, the compounds of the formula (IV) can be prepared by reacting alcohols having two lipophilic chains, of the formula (II), with n molecules of epichlorohydrin, epibromohydrin or tert.-butyl glycidyl ether, in the presence of an acid catalyst and optionally in the presence of a solvent. The acid catalysts are preferably Lewis acid catalysts, such as boron trifluoride, stannic chloride or antimony pentachloride, generally in an amount of 0.2 to 5% by weight, relative to the reaction mixture, and at a temperature from 20° to 120° C. and preferably 50° to 100° C.

If solvents are used, they are chosen more particularly from aromatic hydrocarbons, such as benzene, toluene or xylene, or aliphatic hydrocarbons, such as hexane or heptane. Preferably, the compounds of the formula (IV) are prepared in the absence of a solvent.

In the case where tert.-butyl glycidyl ether is used, it is possible to carry out the polyaddition reaction in the presence of an alkali metal catalyst, such as the methylate, ethylate or tert.-butylate of sodium or potassium, generally at a temperature of 120° to 180° C.

The n molecules of epihalogenohydrin or of tert.-butyl glycidyl ether give rise to the formation of mixtures of compounds containing a number of halogen or tert.-butoxy units which is less than, equal to or greater than the value n, the latter representing a number-average statistical value.

During this reaction, depending on the way in which the epoxide ring opens, it is possible to obtain two structures for the halogen or tert.-butoxy unit, and these are represented by the general formula:

$$+C_2H_3O(CH_2B)+$$

in both cases, and by the structural formulae:

$$\left[\begin{array}{c} CH_2-CH-O \\ | \\ CH_2B \end{array}\right] \qquad (V)$$

$$\left[\begin{array}{c} CH-CH_2-O \\ | \\ CH_2B \end{array}\right] \qquad (VI)$$

Although the presence of units having the structure (V) is more probable, a certain amount of units of the structure (VI) can exist.

In the third step, if A denotes the group OH, the compounds of the formula (I) are prepared from the compounds of the formula (IV):

(1) either by heating the halogen compounds in the presence of sodium acetate or potassium acetate, in a solvent of the glycol or glycol ether type, such as ethylene glycol, propylene glycol or butylene glycol, diethylene glycol or dipropylene glycol, or diethylene glycol butyl ether, typically at a temperature of 180° C. to 190° C. for 3 to 6 hours, and then, after filtering off the inorganic salts and removing the solvents under reduced pressure, by carrying out a saponification reaction in the presence of concentrated sodium hydroxide or potassium hydroxide, or by carrying out an alcoholysis reaction in absolute methanol or ethanol, in the presence of sodium methylate or ethylate or potassium methylate or ethylate, (2) or by heating the polytert.-butoxy derivatives in the presence of a strong acid, such as a sulphocarboxylic acid, sulphuric acid or para-toluenesulphonic acid, at, say, 80°–110° C.

The compounds of the invention in which the group A denotes (b) or (c) can be obtained by reacting thioethanol or thioglycerol with a polyhalogen compound in the presence of sodium hydroxide or potassium hydroxide and in the presence of solvents, such as ethanol, isopropanol, propanol, butanol, ethylene glycol, propylene glycol or butylene glycol, ethylene glycol monomethyl ether, monoethyl ether or monobutyl ether, and optionally water. The polyhydroxylic polythioether compounds can then be oxidised with hydrogen peroxide at a temperature of, say, 25° to 50° C., optionally in the presence of acetic acid or lactic acid.

The two types of structure V and VI lead to the following two structural formulae for the units of the formula (I):

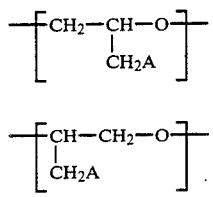

The simultaneous presence of two types of structure in no way detracts from the properties of the products according to the invention.

The compounds of the formula (I), according to the invention, are generally in the form of an oil, a paste or a wax. Depending on the number of carbon atoms in $\underline{R}$ and $R_1$ and depending on the average number of units $\bar{n}$, these compounds are on the whole lipophilic, dispersible in water or completely soluble. Thus, the smaller the number of carbon atoms and the larger the number $\bar{n}$, the greater is the hydrophilicity of the products.

The hydrophilicity and the solubility in water of the compounds according to the invention can be increased either by removing the most lipophilic products by molecular distillation, or by reacting ethylene oxide or glycidol with the hydroxyl groups, it being possible for this reaction to be carried out under the usual conditions, in the presence of acid or alkaline catalysts and optionally in the presence of solvents.

In such a case one or more of the OH group in the substituents represented by A may be replaced by the following groups:

—O—$(C_2H_4O)_r$—H, wherein r varies between 0 and 50.
—O—$[C_2H_3O(CH_2OH)]_s$—H wherein s varies between 0 and 20.

The compounds according to the invention can be used by themselves or in a mixture, in aqueous or aqueous-alcoholic solution or dispersion, in the form of a water-in-oil or oil-in-water emulsion, in the form of a wax or in the form of an aerosol, generally in amounts from 0.05 to 80%, and preferably 0.5 to 50%, relative to the total weight of the composition.

The term aqueous-alcoholic solution is understood as meaning solutions of water and of a lower alcohol such as ethanol, a glycol or a glycol ether.

In particular, the compounds according to the invention can be introduced as a base surface-active agent or as an additive into cosmetic or pharmaceutical compositions which can be presented in the form of an aqueous or aqueous-alcoholic solution or dispersion, a cream, a milk, a compact or a stick, or they can be packaged in the form of aerosols.

The compounds can be used as a cleansing agent for the skin or for the head of hair, as a wetting agent, emulsifying agent, dispersing agent, solubilising agent, superfatting agent or emollient, as a mild and inert excipient or as lipids which are capable of acting as a vehicle for active substances.

Examples of cosmetic compositions which may be mentioned in particular are shampoos, rinses, wavesetting lotions, brushing products, perming or colouring compositions, make-up foundations, lotions for removing eye make-up, milks for removing make-up, body milks, neutral make-up bases, anti-sunburn compositions and antiperspirant or deodorant creams.

In the case where the compounds according to the invention are used in the preparation of lipid vesicles, they may or may not be combined, for the purpose of modifying the permeability of these vesicles, with long-chain alcohols or diols, with sterols, such as cholesterol or sitosterol, and optionally, although this is frequently unnecessary, with positively or negatively charged substances, such as sodium dicetylphosphate or dimethyldioctadecylammonium chloride or bromide.

The fact that it is possible to produce entirely non-ionic lipid vesicles constitutes a great advantage for the compounds of the invention.

The cosmetic or pharmaceutical compositions containing one or more products according to the invention can also contain other constituents, such as non-ionic, anionic, cationic or amphoteric surface-active agents as will be well known to those in the art, animal, mineral or vegetable oils, anionic, cationic, non-ionic or amphoteric resins which are normally used in cosmetics, sun filters, thickeners, opacifying agents, preservatives, perfumes, dyestuffs, lower alcoholic solvents, pH modifiers, inorganic salts, and active substances which can have an action in the treatment, care or protection of the skin or hair.

The following examples further illustrate the present invention.

EXAMPLES OF THE PREPARATION OF THE COMPOUNDS

Preparation of the Compound of Example 2A (a) Preparation of the compound represented by the formula

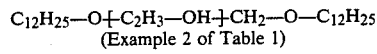

(Example 2 of Table 1)

17 g of a solution of sodium methylate in methanol, containing 6 milliequivalents/g, are added to 558 g (3 mols) of dodecan-1-ol sold under the same Alfol 12. The methanol is removed by heating to 120° C. under reduced pressure. 242 g (1 mol) of dodecyl glycidyl ether are then added in the course of 1 hour 30 minutes, at 150° C., under a nitrogen atmosphere. After heating for 4 hours, the extent of reaction, assessed by determining the residual epoxide groups, is virtually quantitative. The reaction mixture is washed with 3×800 ml of water at 90° C. 170 ml of isopropanol are added in order to facilitate decantation. The organic phase is then heated under reduced pressure. After the excess dodecanol has been removed, the alcohol compound with two lipophilic chains is distilled by molecular distillation at 160° C., under a pressure of $10^{-3}$ mm of mercury.

The compound is in the form of a white wax with a melting point of 40°–41° C.

(b) Preparation of the mixture of compounds corresponding to the formula

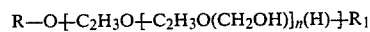

-continued
(Example 2A of Tables 3 and 4)

in which R denotes C$_{12}$H$_{25}$—, R$_1$ denotes C$_{12}$H$_{25}$—O—CH$_2$— and n denotes a statistical value of 5.

0.7 g of BF$_3$ etherate is added to 107 g (0.25 mol) of the compound prepared above, and 115.5 g (1.25 mols) of epichlorohydrin are then added dropwise at 70° C. in the course of 2 hours.

Heating is continued for a further one hour after the addition. The polyhalogen derivative is subsequently washed 3 times with 250 ml of boiling water and then dried.

The resulting product is then taken up in 190 g of dipropylene glycol and 106 g (1.07 mols) of potassium acetate and the mixture is heated at 185° C. for 6 hours, under a nitrogen atmosphere. After filtering off the potassium chloride and distilling the solvent, the product is saponified in the presence of excess 40% strength sodium hydroxide solution and washed 3 times with 200 ml of boiling water, in the presence of primary butanol in order to facilitate the separation of the organic phase. After distillation of the solvents under reduced pressure, a product is obtained in the form of a brown oil which is soluble in vaseline oil (VO—liquid petrolatum) and dispersible in water.

The cloud point, measured at an active ingredient concentration of 5% in a 25% strength solution of butyldiglycol (BDG) in water, is 82° C.

Preparation of the Compound of Example 5A

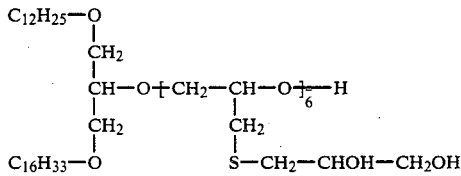

0.54 ml of SnCl$_4$ is added to 48.4 g (0.1 mol) of the molten intermediate 5, obtained in accordance with the process described in Table 1. The mixture is heated to 100° C. and 57.5 g (0.6 mol) of epichlorohydrin are then added dropwise. The mixture is kept at 100° C. for a further 1 hour 30 minutes after the addition has ended. The reaction is then virtually complete.

100 g of cellosolve and 63 g (0.58 mol) of thioglycerol are added to 101 g (580 milliequivalents of chlorine) of the polychlorinated product thus obtained. The reaction mixture is heated to 100° C. and 58 g (0.58 mol) of 40% strength sodium hydroxide solution are then added dropwise.

After heating for 3 hours at 100°–105° C., 230 g of butan-1-ol are added and the reaction mixture is washed twice with about 500 ml of boiling water. The organic phase is then heated under reduced pressure in order to remove the solvents.

This yields an amber-coloured paste which is dispersible in water. The cloud point, measured at an active ingredient concentration of 5% in a 25% strength solution of BDG in water, is above 100° C.

Preparation of the Compound of Example 5B

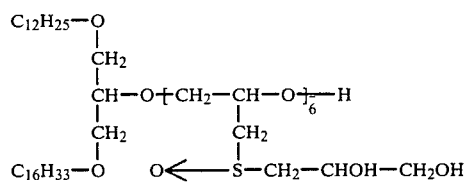

12.2 ml of hydrogen peroxide of 158.6 volumes strength are added dropwise to 50 g (171 milliequivalents of thioether groups) of the product described in Example No. 5A, dissolved in 50 ml of methanol.

The temperature is kept at between 30° and 45° C. for 1 hour 30 minutes after the addition has ended.

After 24 hours at ambient temperature, 200 mg of SO$_3$Na$_2$ are added in order to destroy the unreacted hydrogen peroxide, and the methanol and the water are then distilled under reduced pressure.

The product thus obtained is a translucent paste which is soluble in water.

Preparation of the Compound of Example 6A

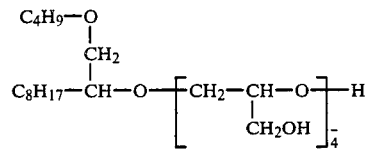

3 ml of a solution of sodium methylate in methanol, containing 6 milliequivalents/g (18 milliequivalents), are added to 34.5 g (0.15 mol) of the intermediate prepared in accordance with the process described in Example 2.

The methanol is distilled under reduced pressure and the temperature is then raised to 155° C. 78 g (0.6 mol) of tert.-butyl glycidyl ether are then added dropwise. After the addition has ended, the mixture is left for a further ¾ hour at 160° C. and the resulting product is then washed 3 times with its own weight of water, in the presence of dilute HCl. It is dried by heating under reduced pressure. 1 g of sulphoacetic acid is then added and the mixture is heated at 100°–110° C. for 2 hours 30 minutes. The evolution of gaseous isobutylene is observed.

The resulting product is dissolved in 70 g of butan-1-ol and the solution is then washed twice with 150 ml of boiling water.

After drying by heating under reduced pressure, a brown liquid which is soluble in water is obtained.

An aqueous solution having an active ingredient concentration of 5% is limpid and viscous.

The cloud point, measured at a concentration of 0.5% in demineralised water, is 70° C.

The compounds which are indicated in the following tables, and the characteristics of which are shown in Tables 1 to 4, are prepared in the same manner as in the preparation examples indicated above.

Tables 1 and 2 relate to the preparation of compounds corresponding to the formula (II). These tables show the nature, the weight and the molar amount of the alcohol and of the compound of the formula (III) used, the nature and the amount of the catalyst, the reaction temperature and the characteristics of the resulting product corresponding to the general formula (II).

Table 3 relates to the preparation of the compounds corresponding to the formula (I) via the compound of the formula (IV). This table defines the nature, the weight and the molar amount of the compound (II) and of the epoxide used, the average value $\bar{n}$ of the number of halogen or tert.-butoxy units, the nature of the catalyst, the amount used and the reaction temperature, the hydrolysis catalyst in the case of tert.-butoxy groups, the solvent and the type of treatment (alcoholysis or saponification) for the polyhalogen derivatives.

Table 4 summarises the physical properties of the compounds of the formula (I) obtained in accordance with one of the processes described in the examples for the preparation of the compounds 2A, 5A or 6A.

In these tables, the abbreviations and symbols have the following meanings:

MeONa denotes a solution of sodium methylate in methanol, containing 6 milliequivalents/g;
iso-$C_8H_{17}$ denotes a 2-ethylhexyl group;
iso-$C_{16}H_{33}$ denotes a 2-hexyldecyl group;
epi denotes epichlorohydrin;
S denotes soluble;
I denotes insoluble;
D denotes dispersible;
T denotes turbid;
\* denotes the cloud point at a concentration of 5% in a 25% strength solution of butyldiglycol in water;
\*\* denotes the cloud point at a concentration of 0.5% in water;
S\* denotes soluble after removal of the volatile compounds by molecular distillation;
BDG denotes butyldiglycol;
DEG denotes diethylene glycol;
DPG denotes dipropylene glycol;
Bp indicates the boiling point;
Mp indicates the melting point;
TBGE denotes tert.butyl glycidyl ether

TABLE 1

| | | Compounds (II) | | | | |
|---|---|---|---|---|---|---|
| | | ROH | | | $R_1$—CH——CH$_2$ (III) \\ O / | |
| Example | R | Weight | Mols | $R_1$ | Weight (g) | Mols |
| 1 | $C_8H_{17}$ | 271 | 2.1 | $C_{16}H_{33}$—O—CH$_2$— | 238.5 | 0.8 |
| 2 | $C_{12}H_{25}$ | 558 | 3 | $C_{12}H_{25}$—O—CH$_2$— | 242 | 1 |
| 3 | $C_{16}H_{33}$ | 485 | 2 | iso-$C_8H_{17}$—O—CH$_2$— | 186 | 1 |
| 4 | iso-$C_{16}H_{33}$ | 435.5 | 1.8 | iso-$C_8H_{17}$—O—CH$_2$— | 111.5 | 0.6 |
| 5 | $C_{16}H_{33}$ | 726 | 3 | $C_{12}H_{23}$—O—CH$_2$— | 242 | 1 |

| | Catalyst | | | Characteristics | | |
|---|---|---|---|---|---|---|
| Example | Nature | Weight (g) | $\theta$ in °C. | Bp in °C./pressure in mm Hg | Mp in °C. | OH number meq/g |
| 1 | MeONa | 13.5 | 150 | 160/10$^{-3}$ | 35 | 2.3 |
| 2 | MeONa | 17 | 150 | 165/10$^{-3}$ | 41 | 2.4 |
| 3 | MeONa | 4.8 | 150 | 160–185/5.10$^{-2}$ | 13 | 2.2 |
| 4 | MeONa | 10.2 | 150 | 165/5.10$^{-2}$ | <−10 | |
| 5 | MeONa | 17 | 140 | 210/10$^{-3}$ | 41 | |

TABLE 2

| | | Compounds (II) | | | | |
|---|---|---|---|---|---|---|
| | | ROH | | | $R_1$—CH——CH$_2$ (III) \\ O / | |
| Example | R | Weight | Mols | $R_1$ | Weight (g) | Mols |
| 6 | $C_4H_8$ | 370 | 5 | $C_8H_{17}$ | 156 | 1 |
| 7 | $C_{10}H_{21}$ | 474 | 3 | $C_{10}H_{21}$ | 184 | 1 |
| 8 | $C_8H_{17}$ | 390 | 3 | $C_{16}H_{33}$ | 268 | 1 |
| 9 | iso-$C_8H_{17}$ | 390 | 3 | $C_{16}H_{33}$ | 268 | 1 |
| 10 | $C_{10}H_{21}$ | 711 | 4.5 | $C_{14}H_{29}$ | 360 | 1.5 |
| 11 | $C_{12}H_{25}$ | 558 | 3 | $C_{12}H_{25}$ | 212 | 1 |
| 12 | $C_{12}H_{25}$ | 279 | 1.5 | $C_{16}H_{33}$ | 135 | 0.5 |
| 13 | $C_{14}H_{29}$ | 642 | 3 | $C_{14}H_{29}$ | 240 | 1 |
| 14 | iso-$C_{16}H_{33}$ | 363 | 1.5 | $C_{12}H_{25}$ | 106 | 0.5 |
| 15 | $C_{18}H_{37}$ | 648 | 2.4 | $C_{10}H_{21}$ | 147 | 0.8 |
| 16 | $C_{16}H_{33}$ | 435.5 | 1.8 | $C_{16}H_{33}$ | 162 | 0.6 |
| 17 | iso-$C_{16}H_{33}$ | 290 | 1.2 | $C_{16}H_{33}$ | 107 | 0.4 |

| | Catalyst | | | Characteristics | | |
|---|---|---|---|---|---|---|
| Example | Nature | Weight (g) | $\theta$ in °C. | Bp in °C./pressure in mm Hg | Mp in °C. | OH number meq/g |
| 6 | Na | 1 | 100 | 98/10$^{-2}$ | | |
| 7 | t-BuOK | 10 | 150 | 165/5.10$^{-2}$ | 46 | |
| 8 | MeONa | 8.5 | 150 | 193–205/8.10$^{-2}$ | 49 | |
| 9 | MeONa | 8.5 | 145 | 190/5.10$^{-2}$ | 24 | 2.4 |
| 10 | MeONa | 12.8 | 140 | 190/5.10$^{-2}$ | 50 | 2.4 |
| 11 | MeONa | 8.5 | 145 | 190–205/10$^{-1}$ | 59 | 2.5 |
| 12 | MeONa | 4.5 | 145 | 210–215/10$^{-3}$ | 58 | |
| 13 | MeONa | 8.5 | 145 | 245/3.10$^{-1}$ | 69 | 2 |
| 14 | MeONa | 8.5 | 150 | 200/10$^{-3}$ | | |
| 15 | MeONa | 8.5 | 150 | | | 2.2 |
| 16 | MeONa | 5 | 145 | 250/10$^{-3}$ | | |
| 17 | MeONa | 12 | 145 | 187/10$^{-3}$ | | |

TABLE 3

| | | Compound (II) | | Expoxide | | |
|---|---|---|---|---|---|---|
| Example | Ex-ample | Amount (g) | Mols | Name | Amount (g) | Mols | $\bar{n}$ |
| 1A | 1 | 107 | 0.25 | TBGE | 260 | 2 | 8 |
| 2A | 2 | 107 | 0.25 | epi | 115.5 | 1.25 | 5 |
| 3A | 3 | 95.5 | 0.2 | epi | 55.5 | 0.6 | 3 |
| 3B | 3 | 30.8 | 0.07 | epi | 32.5 | 0.35 | 5 |
| 3C | 3 | 110 | 0.25 | epi | 185 | 2 | 8 |
| 3D | 3 | 110 | 0.25 | epi | 185 | 2 | 8 |
| | | | | glycidol | 74 | 1 | 4 |
| 4A | 4 | 34.2 | 0.08 | TBGE | 31.2 | 0.24 | 3 |
| 5A | 5 | 48.4 | 0.1 | epi | 57.5 | 0.6 | 6 |
| 5B | 5 | 48.4 | 0.1 | " | 57.5 | 0.6 | " |
| 6A | 6 | 34.5 | 0.15 | TBGE | 78 | 0.6 | 4 |
| 7A | 7 | 102.5 | 0.3 | epi | 111 | 1.2 | 4 |
| 8A | 8 | 99.5 | 0.25 | epi | 115.5 | 1.25 | 5 |
| 8B | 8 | 67.5 | 0.17 | epi | 157.3 | 1.7 | 10 |
| 9A | 9 | 21.3 | 0.05 | epi | 13.8 | 0.15 | 3 |
| 9B | 9 | 17 | 0.04 | epi | 18.5 | 0.2 | 5 |

TABLE 3-continued

Compounds (I)

| Ex | | | | | | | |
|---|---|---|---|---|---|---|---|
| 9C | 9 | 42.5 | 0.1 | epi | 74 | 0.8 | 8 |
| 9D | 9 | 42.5 | 0.1 | epi | 74 | 0.8 | 8 |
| | | | | glycidol | 51.8 | 0.7 | 7 |
| 10A | 10 | 159 | 0.4 | epi | 74 | 0.8 | 2 |
| 10B | 10 | 119.5 | 0.3 | epi | 111 | 1.2 | 4 |
| 10C | 10 | 79 | 0.2 | epi | 92.5 | 1 | 5 |
| 10D | 10 | 99.5 | 0.25 | epi | 162 | 1.75 | 7 |
| 10E | 10 | 59.2 | 0.15 | epi | 111 | 1.2 | 8 |
| 10F | 10 | 99.5 | 0.25 | epi | 208 | 2.25 | 9 |
| 10G | 10 | 79.5 | 0.2 | epi | 185 | 2 | 10 |
| 10H | 10 | 119.5 | 0.3 | epi | 333 | 3.6 | 12 |
| 11A | 11 | 119.5 | 0.3 | epi | 138.7 | 1.5 | 5 |
| 12A | 12 | 90.8 | 0.2 | epi | 111 | 1.2 | 6 |
| 13A | 13 | 45.5 | 0.1 | epi | 55.5 | 0.6 | 6 |
| 14A | 14 | 25 | 0.055 | epi | 30.6 | 0.33 | 6 |
| 15A | 15 | 59 | 0.13 | epi | 72.2 | 0.78 | 6 |
| 16A | 16 | 76.5 | 0.15 | TBGE | 78 | 0.6 | 4 |
| 17A | 17 | 49.5 | 0.1 | epi | 62.5 | 0.7 | 7 |

| Example | Catalyst Nature | A- mount (g) | $\theta$ °C. | Catalyst | Hydrolysis Solvent | Alcoholysis/ saponification |
|---|---|---|---|---|---|---|
| 1A | MeONa | 4 | 150 | sulpho-palmitic acid 1.5% | — | — |
| 2A | BF$_3$ | 0.7 | 70 | — | BDG | saponification |
| 3A | BF$_3$ | 0.4 | 75 | — | DPG | alcoholysis |
| 3B | BF$_3$ | 0.15 | 75 | — | " | " |
| 3C | BF$_3$ | 1.2 | 75 | — | " | " |
| 3D | BF$_3$ | 1.2 | 75 | — | " | — |
| | MeONa | 0.2 | 150 | | | |
| 4A | t-BuOK | 6 | 150 | sulpho-palmitic acid 2.5% | — | — |
| 5A | SnCl$_4$ | 0.54 | 100 | — | — | — |
| 5B | " | 0.54 | " | — | MeOH | oxidation |
| 6A | MeONa | 3 | 155 | sulpho-acetic acid 1g | — | — |
| 7A | BF$_3$ | 0.6 | 75 | — | DPG | alcoholysis |
| 8A | BF$_3$ | 0.6 | 70 | — | DPG | alcoholysis |
| 8B | BF$_3$ | 1.3 | 70 | — | " | " |
| 9A | BF$_3$ | 0.1 | 75 | — | DEG | " |
| 9B | BF$_3$ | 0.1 | 75 | — | DPG | " |
| 9C | BF$_3$ | 0.5 | 75 | — | DPG | " |
| 9D | BF$_3$ | 0.5 | 75 | — | " | " |
| | MeONa | 0.3 | 150 | — | — | — |
| 10A | BF$_3$ | 0.6 | 55 | — | DEG | saponification |
| 10B | BF$_3$ | 0.6 | 55 | — | BDG | " |
| 10C | BF$_3$ | 0.5 | 75 | — | DPG | alcoholysis |
| 10D | BF$_3$ | 1 | 55 | — | DPG | saponification |
| 10E | BF$_3$ | 0.7 | 75 | — | " | alcoholysis |
| 10F | BF$_3$ | 1.2 | 55 | — | DPG | saponification |
| 10G | SnCl$_4$ | 2.5 | 100 | — | " | " |
| 10H | BF$_3$ | 1.8 | 55 | — | DPG | alcoholysis |
| 11A | BF$_3$ | 0.8 | 70 | — | DPG | alcoholysis |
| 12A | BF$_3$ | 0.6 | 70 | — | " | " |
| 13A | BF$_3$ | 0.4 | 75 | — | DPG | " |
| 14A | BF$_3$ | 0.2 | 75 | — | " | " |
| 15A | BF$_3$ | 0.4 | 55 | — | " | saponification |
| 16A | MeONa | 2.4 | 150 | sulpho-palmitic acid 2.5% | — | — |
| 17A | BF$_3$ | 0.5 | 60 | — | DPG | alcoholysis |

REMARK:
In examples 3D and 9D the glycidol is reacted at the end of the preparation with the OH groups.

TABLE 4

Physical properties of the compounds (I)

| Example | Appearance | Cloud point | Solubility vaseline oil | water |
|---|---|---|---|---|
| 1A | dark brown paste | >100* | | D |
| 2A | brown oil | 82* | S | D |
| 3A | yellow oil | 67* | S | I |
| 3B | brown oil | 88* | T | D |
| 3C | light brown paste | >100* | sparingly S | D |
| 3D | light brown paste | >100** | I | S |
| 4A | black oil | 61* | | I |
| 5A | soft amber paste | >100* | | D |
| 5B | light yellow paste | | | S |
| 6A | brown oil | 70** | I | S |
| 7A | brown oil | 80* | S | I |
| 8A | light brown paste | 86* | sparingly S | D |
| 8B | brown paste | >100** | I | S* |
| 9a | light brown oil | 72* | S | I |
| 9B | light brown oil | 87* | S | D |
| 9C | yellow paste | >100* | sparingly S | D |
| 9D | amber paste | >100** | I | S |
| 10A | light brown oil | (I*) | S | I |
| 10B | amber oil | 74* | S | D |
| 10C | brown paste | 87* | S | D |
| 10D | brown paste | 93* | S | D |
| 10E | brown paste | >100* | | D |
| 10F | light brown paste | >100* | sparingly S | D |
| 10G | brown paste | >100* | I | D |
| 10H | brown paste | >100* | I | S |
| 11A | brown paste | | | D |
| 12A | brown paste | ≈100* | S | D |
| 13A | light brown paste | 94* | S | D |
| 14A | brown paste | 91* | S | D |
| 15A | brown paste | 93* | S | D |
| 16A | chestnut wax | >100* | | I |
| 17A | light brown paste | 90* | sparingly S | D |

The following examples illustrate the use of the compounds according to the invention in cosmetic formulations.

COMPOSITION 1

Neutral Make-up Base (Oil-in-Water Emulsion)

Oil of the formula: 22 g

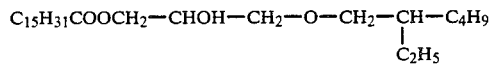

$$C_{15}H_{31}COOCH_2-CHOH-CH_2-O-CH_2-CH-C_4H_9$$
$$|$$
$$C_2H_5$$

Compound of Example 3C, of the formula: 7 g

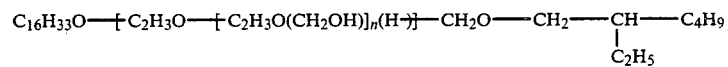

$$C_{16}H_{33}O-[C_2H_3O-[C_2H_3O(CH_2OH)]_n(H)]-CH_2O-CH_2-CH-C_4H_9$$
$$|$$
$$C_2H_5$$

in which e,ovs/n/ =8
Perfume and preservative: q.s.
Stile demineralised water: q.s.p. 100 g

COMPOSITION 2

Night Cream (Water-in-Oil Emulsion)

Isopropyl myristate: 40 g
Compound of Example 9B, of the formula: 10 g

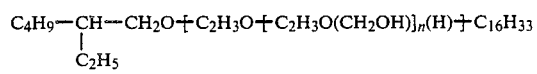

$$C_4H_9-CH-CH_2O-[C_2H_3O-[C_2H_3O(CH_2OH)]_n(H)-C_{16}H_{33}$$
$$|$$
$$C_2H_5$$

in which $\bar{n}=5$
Perfume and preservative: q.s.
Sterile demineralised water: q.s.p. 100 g

COMPOSITION 3

Body Milk (Oil-in-Water Emulsion)

Codex vaseline oil: 30 g
Compound of Example 8A, of the formula: 7 g

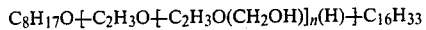
$C_8H_{17}O\text{-}[C_2H_3O\text{-}[C_2H_3O(CH_2OH)]_n(H)]\text{-}C_{16}H_{33}$ in which $\bar{n} = 5$
Perfume and preservative: q.s.
Sterile demineralised water: q.s.p. 100 g

COMPOSITION 4

Skin-Care Cream (Oil-in-Water Emulsion)

Sweet-almond oil: 40 g
Compound of Example 10D, of the formula: 10 g

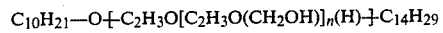
$C_{10}H_{21}\text{—O}\text{-}[C_2H_3O[C_2H_3O(CH_2OH)]_n(H)]\text{-}C_{14}H_{29}$ in which $\bar{n} = 7$
Perfume and preparative: q.s.
Sterile demineralised water: q.s.p. 100 g

COMPOSITION 5

Lotion for Removing Eye Make-up

Compound of Example 8B, of the formula: 4 g

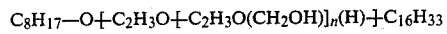
$C_8H_{17}\text{—O}\text{-}[C_2H_3O\text{-}[C_2H_3O(CH_2OH)]_n(H)]\text{-}C_{16}H_{33}$ in which $\bar{n} = 10$
Hexylene glycol: 1 g
Allantoin: 0.05 g
Potassium dihydrogen phosphate: 0.1 g
Dipotassium hydrogen phosphate.$3H_2O$: 0.4 g
Sodium ethyl-mercurithiosalicylate: q.s.
Sterile demineralised water: q.s.p. 100 g
Perfume: q.s.

COMPOSITION 6

Moisturising Composition 2 g of the compound of Example 10C are mixed with 5 g of a 3% strength aqueous solution of glycerol.

After homogenisation for 30 minutes using an ultra-dispenser, a dispersion of small spheres is obtained.

COMPOSITION 7

Anti-sunburn Composition 4.8 g of the compound 13A and 3.2 g of cholesterol are intimately mixed at a temperature of 90° C.

20 g of a 4% strength aqueous solution of polyoxyethyleneated para-aminobenzoic acid containing 25 mols of ethylene oxide are then added.

The mixture is allowed to return to ordinary temperature, whilst stirring, and a further 72 g of the 4% strength aqueous solution of para-aminobenzoic acid containing 25 mols of ethylene oxide are then added.

After homogenisation for 30 minutes using an ultradispenser, small spheres are obtained, the average size of which is approximately one micron.

We claim:

1. A non-ionic surface-active product having the formula

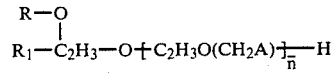
$$\begin{array}{c} R\text{—O} \\ | \\ R_1\text{—}C_2H_3\text{—}O\text{-}[C_2H_3O(CH_2A)]_{\bar{n}}\text{—H} \end{array}$$

wherein
R represents a linear or branched, saturated or unsaturated aliphatic radical containing 4 to 20 carbon atoms,
$R_1$ represents (1) a linear or branched alkyl radical, (2) a linear or branched alkoxymethyl radical or (3) an alkenyloxymethyl radical, wherein the alkyl or alkenyl moieties contain from 4 to 20 carbon atoms, R and $R_1$ containing a total of 12 to 38 carbon atoms,
$\bar{n}$ represents an average statistical value of 2 to 20,
A represents a member selected from the group consisting of (a) OH,

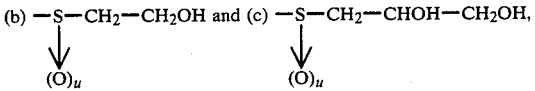
(b) $-S-CH_2-CH_2OH$ and (c) $-S-CH_2-CHOH-CH_2OH$,
       $\downarrow$                          $\downarrow$
       $(O)_u$                               $(O)_u$ wherein u represents 0 or 1, and $C_2H_3$ represents

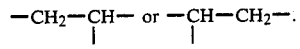
$-CH_2-CH-$ or $-CH-CH_2-$.
       |              |

2. The product of claim 1 wherein R represents butyl, hexyl, octyl, decyl, dodecyl, tetradecyl, hexadecyl, octadecyl, 2-ethylhexyl or 2-hexadecyl.

3. The product of claim 2 wherein $R_1$ represents hexyl, octyl, decyl, dodecyl, tetradecyl, hexadecyl or octadecyl, or an alkoxymethyl radical derived therefrom, or 2-ethylhexyloxymethyl, 2-hexyldecyloxymethyl or 2-octyldodecyloxymethyl.

4. A cosmetic composition for the care and treatment of the skin or hair comprising in a cosmetically acceptable carrier or vehicle an effective amount of the product of claim 1.

5. The cosmetic composition of claim 4 in the form of a dispersion of lipid vesicles wherein the wall of said vesicles consists of said product.

6. A pharmaceutical composition for the care and treatment of the skin or hair comprising in a pharmaceutically acceptable carrier or vehicle an effective amount of the product of claim 1.

* * * * *